US007286630B2

(12) United States Patent
Holt

(10) Patent No.: US 7,286,630 B2
(45) Date of Patent: Oct. 23, 2007

(54) METHOD AND APPARATUS FOR FACILITATING ENHANCED CT SCANNING

(75) Inventor: Kevin Holt, Chicago, IL (US)

(73) Assignee: Varian Medical Systems Technologies, Inc., Palo Alto, CA (US)

( * ) Notice: Subject to any disclaimer, the term of this patent is extended or adjusted under 35 U.S.C. 154(b) by 0 days.

(21) Appl. No.: 11/305,750

(22) Filed: Dec. 16, 2005

(65) Prior Publication Data

US 2007/0140412 A1  Jun. 21, 2007

(51) Int. Cl.
*A61B 6/00* (2006.01)
(52) U.S. Cl. ............................................. 378/8; 378/20
(58) Field of Classification Search .................... 378/4, 378/20, 62, 207, 8
See application file for complete search history.

(56) References Cited

U.S. PATENT DOCUMENTS 4,989,225 A * 1/1991 Gupta et al. .................. 378/10
5,648,996 A * 7/1997 Gupta ............................ 378/4

\* cited by examiner

*Primary Examiner*—Courtney Thomas
(74) *Attorney, Agent, or Firm*—Fitch, Even, Tabin & Flannery

(57) ABSTRACT

A method of and apparatus for facilitating enhanced computed tomography ("CT") scanning is provided including a scanned object (130) disposed on a translating table (120) capable of rotating the object (130) and moving the through the CT system (100). Certain values regarding the scanning system geometry and a target metric are provided (510 and 520). Given these values and the target metric, the system determines (530) a scanning procedure as a predetermined function of the target metric and the scanning system geometry dependant values. Further, the system may resample (720) the scanning data into an output array according to a predetermined sampling algorithm.

9 Claims, 6 Drawing Sheets

METHOD AND APPARATUS FOR FACILITATING ENHANCED CT SCANNING

TECHNICAL FIELD

This invention relates generally to the field of computed tomography ("CT") scanning systems and more particularly to CT scanning systems that take data through a combination of rotational and translational motion.

BACKGROUND

Computed tomography ("CT" or "CAT") scanning systems are generally known in the art. The first CT scanners used a source of X-rays directed as a beam and a single detector to detect the amount of X-rays passing through the scanned object. During a scan of an object, the source and detector are passed through a line on the object, then the source and detector are moved relative to the object and scanned through another line on the object.

So called "second-generation" CT scanners use a fan-shaped X-ray beam and a corresponding plurality of detectors arranged along the fan. Similar to earlier CT scanners, a second-generation CT scanner may be moved relative to the scanned object to collect a full set of readings on the object. In between scans, the object may be rotated to expose a different portion of the object to the X-ray source. Usually, this rotation amount is close to or equal to the total angle spanned by the X-ray fan. In other prior scanners, the object may be rotated during translation or movement across the scanner.

So called "third-generation" CT scanners also use a fan-shaped (or cone-shaped) X-ray beam and a corresponding plurality of detectors arranged along the fan. In contrast to second-generation CT scanners, a third-generation CT scanner collects data many times during a full rotation of the scanned object, typically without translation or movement of the object across the scanner.

For any typical CT scanner, data is collected from each scan or view of the scanned object into an array that is manipulated by a computer to provide a variety of images of the object. These provided images are called reconstructions or reconstructed images. Several known algorithms exist for creating the reconstructed images of an object scanned by CT scanners. These algorithms use various geometric values relating to the physical CT scanning system to manipulate the collected scan data into the reconstructed images.

A common goal for imaging systems, such as CT scanning systems, is to provide images with the highest resolution possible. The resolution of a given system is limited by the effective beam width, which is dependant on the geometry of the system, and on the X-ray sampling. When the beam width is large, the image appears smeared and high-frequency detail is reduced. When the sample spacing is large, the high-frequency detail is lost altogether. Nyquist's criterion, applied to CT, says that to prevent losing any information due to sampling, the sample spacing should be less than half of the reciprocal of the highest frequency left in the data after it has been blurred by the beam width. To a first-degree approximation, this means that for good sampling, the sample spacing should be at most half the effective beam width, though to a lesser extent performance can be further improved by having even finer sampling. Conventional third-generation scanners inherently violate Nyquist's criterion and therefore have especially poor X-ray sampling. The reason for this is because for third generation, the sample spacing is the same as the detector pitch, and the detector pitch is inherently at least as large as the effective beam width.

One known method to get good X-ray sampling is to use second-generation scanning, where one can get good sampling by choosing the translation increment to be smaller than the effective beam width by an arbitrary amount. Second-generation scanning, however, is fairly inefficient because during much of the scan time the scan object is in positions where a significant portion of the X-ray beam does not intersect the scan object.

There are also several known methods for improving the sampling of a third-generation scan. One known method is to position the rotation-axis in such a place that the projection of the rotation axis onto the detector is exactly one quarter of the way between two neighboring detector elements. This method, however, requires that when changing slice positions, the rotation axis does not move from side to side. For medical geometries, where the source and detector are on a rotating assembly and the patient is fed through the middle, it is feasible to keep the rotation axis at a fixed location relative to the source and detector. For industrial geometries where the table rotates relative to a fixed source and detector, however, the table may shift from side-to-side as it is raised or lowered. Thus, the position of the rotation axis within the scanning plane may change with table height, and it is rather difficult to maintain the quarter-detector constraint on the rotation axis for all table elevation-positions. Furthermore, even if the position of the rotation axis can be forced to remain constant, this method can at best double the sampling of conventional CT—it typically cannot be extended to give further improvement.

Another known method to improve the sampling of a third generation scan is to use multiple X-ray sources, either by switching between multiple independent sources, or by moving the focal spot of a single source between multiple positions by means of electromagnetic deflection. X-ray sources with multiple focal spots, however, can be prohibitively expensive, and care must be taken to synchronize the source-switching with the detector sampling times.

Another known method to improve the sampling of a third generation scan is to take multiple scans, each with the detector in a slightly shifted position relative to the scanned object, then interleave the data from the scans. Many scanners, however, are not built with a detector motion axis, and for interleaving to produce mathematically correct data, the detector must be kept focused on the source.

Another known method to increase the X-ray sampling in a third-generation CT scanning system is to interleave data from two or more scans where the object has been rotated and/or translated effectively a fraction of a beam width. Interleaving, however, fails to provide mathematically correct data arrays in the case of translating the object with a flat detector array, with or without rotation, or, in the case of translating the object with a curved detector array, without rotation. For these cases when interleaving does not produce mathematically correct images, only a small number of scans may be interleaved before the maximum benefit of doing so is realized. The case where interleaving is indeed mathematically correct is where the object is shifted while simultaneously rotating it a fraction of an angular detector pitch. For systems with heavy objects, dense detector arrays, and/or a small fan angle, mechanical limitations can make the required small precise rotation rather difficult to achieve physically.

Another goal of CT scanning systems is to perform scans at the highest possible speed to improve the throughput of the scanner when scanning objects or to decrease the time for the scanning of a patient. Often, speed and resolution are incompatible goals where speed must be sacrificed for higher resolution and vice versa. Typically, third-generation scanning is used when high speed is the top priority, whereas second-generation scanning is often used when high resolution is the top priority. Ideally, the benefits of both scanning methods should be realized.

BRIEF DESCRIPTION OF THE DRAWINGS

The above needs are at least partially met through provision of the method and apparatus for facilitating enhanced CT scanning described in the following detailed description, particularly when studied in conjunction with the drawings, wherein.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will further be appreciated that certain actions and/or steps may be described or depicted in a particular order of occurrence while those skilled in the arts will understand that such specificity with respect to sequence is not actually required. It will also be understood that the terms and expressions used herein have the ordinary meaning as is accorded to such terms and expressions with respect to their corresponding respective areas of inquiry and study except where specific meanings have otherwise been set forth herein.

DETAILED DESCRIPTION

Generally speaking, pursuant to these various embodiments, a method of and apparatus for facilitating enhanced computed tomography ("CT") scanning is provided including a scanned object disposed on a translating table capable of rotating the object and moving the object through the CT system. Certain values regarding the scanning system geometry and a target metric are provided. Given these values and the target metric, the system determines a scanning procedure as a predetermined function of the target metric and the scanning system geometry dependant values. Further, the system may resample the scanning data into an output array according to a predetermined sampling algorithm.

The scanning system facilitates scanning at an increased resolution with a minimally increased scan time. Further, the strict scanning geometries called for in other known methods for increasing X-ray sampling in a third-generation scanning system are not needed when implementing certain embodiments described herein.

Figure 1:
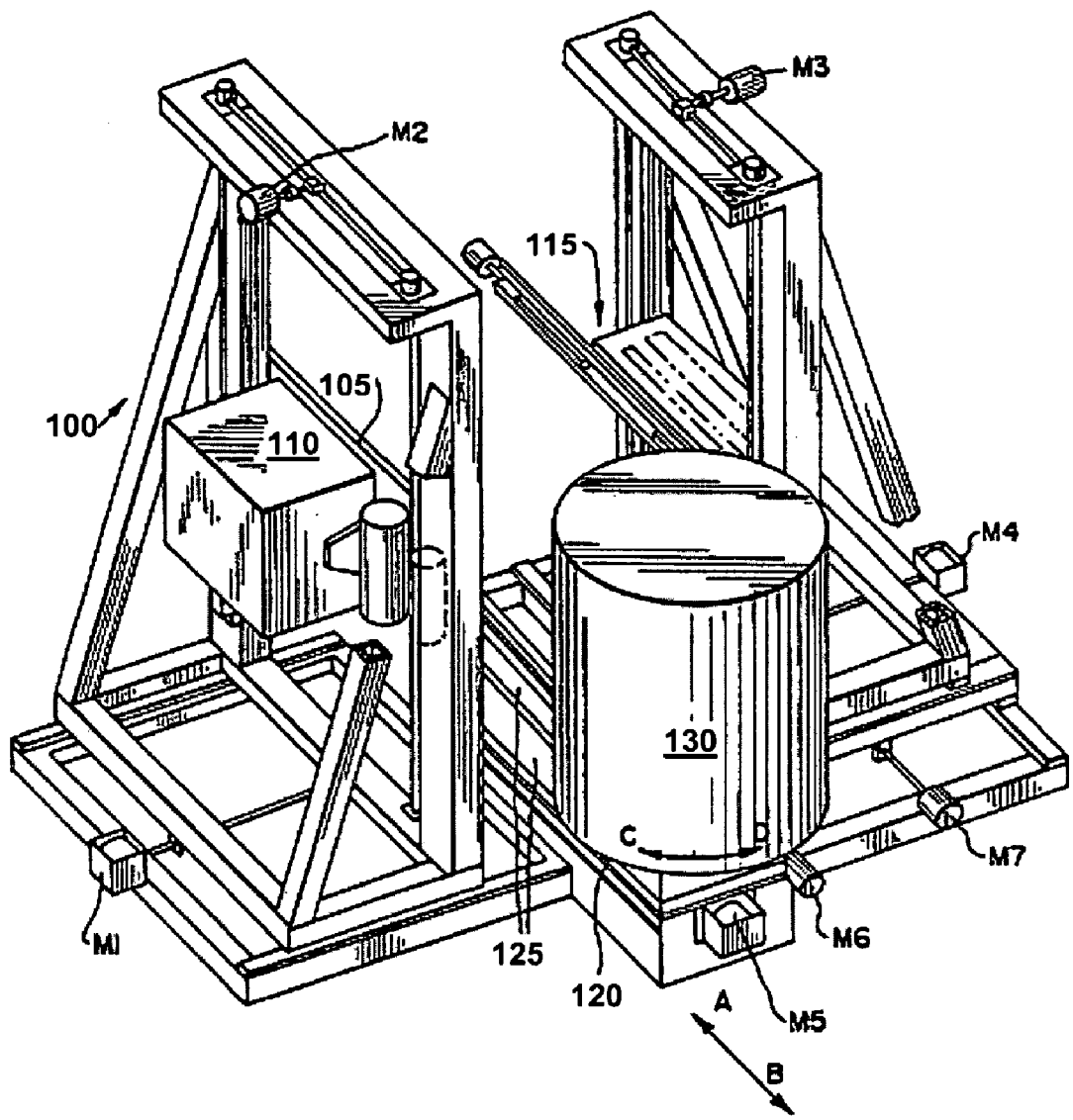
FIG. 1 is a perspective view of a CT scanning system as configured in accordance with various embodiments of the invention.

Referring now to the drawings, and in particular to FIG. 1, a CT scanning system 100 is provided, including a frame 105 for supporting an X-ray source 110 and a detector 115 disposed opposite the X-ray source 110. A translating table 120 is capable of rotating an object 130 as indicated by the line C-D and moving the object 130 between the X-ray source 110 and the detector 115 along tracks 125 in the direction indicated by the line A-B. The frame 100 includes a plurality of motors M1, M2, M3, M4, M5, M6, and M7 for moving the various parts including the source 110, detector 115, and/or translating table 120 relative to one another to conduct various scans. The number and/or placement of the motors may be changed to fit a given application. One skilled in the art will recognize that the object 130 may remain stationary or the source 110 and/or the detector 115 may remain stationary to effect relative movement, translation or rotation, during a scan. One skilled in the art will also recognize that the general construction of the CT scanning system 100 as depicted is an example of a typical second-generation scanner and the invention as described herein may be practiced with modified second- or third-generation systems or other types of CT scanners.

Figure 2:
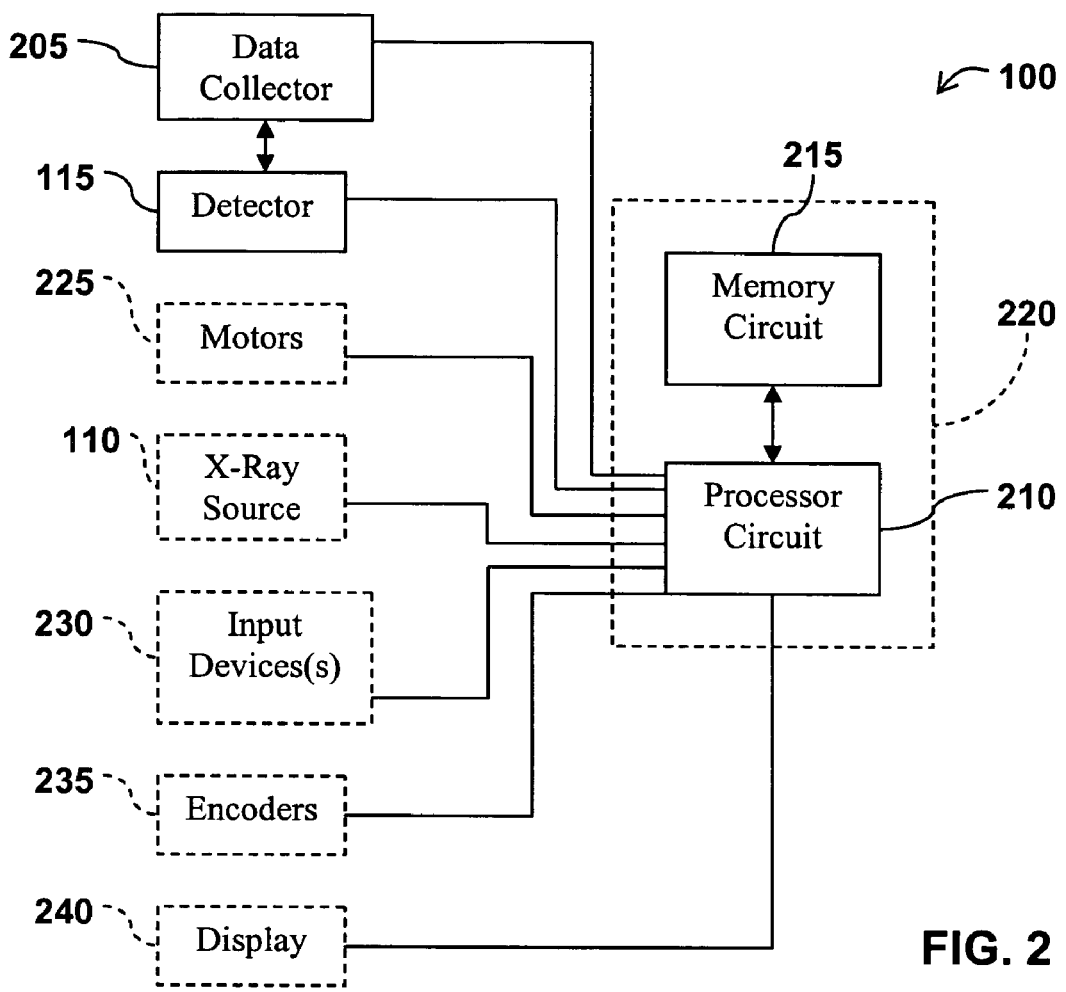
FIG. 2 is a block diagram of a CT scanning system as configured in accordance with various embodiments of the invention.

With reference now to FIG. 2, a data collector 205 is operably coupled to the detector 115 that collects data. The data collector 205 may be a hardware device directly coupled to the detector 115 for creating signals to send to a processor circuit 210, or the data collector 205 may be other hardware and associated enabling software otherwise operably connected to the detector 115 and processor circuit 210. A memory circuit 215 stores geometry dependant values regarding the CT scanning system 100 and a target metric. The memory circuit 215 also may store data from the data collector 215 regarding the scans performed by the system 100. The target metric may be either a target resolution or a target scan time for a particular scan.

The processor circuit 210 is associated with the data collector 205 and the memory circuit 215 and determines a CT scanning procedure according to a predetermined function of the target metric and the CT scanning system geometry dependant values. The memory circuit 215 and processor circuit 210 may be incorporated into a single computing device or automatic calibrator 220, such as a personal computer with enabling software, that is operably coupled to the other devices or elements. The details of such a coupling are known in the art and are therefore omitted here for the sake of brevity. For instance, the motors, collectively indicated as 225, and the X-ray source may be controlled by the processor circuit 210 and associated software. The X-ray source may be 150 KV or 420 KV tube, a 2 MeV linear accelerator, or other appropriate source of imaging radiation including known and appropriate focusing and/or collimating apparatuses and shielding. Further, an input device 230 such as a keyboard and/or mouse may be provided for the automatic calibrator 220 for providing certain inputs and/or values for controlling the system 100. Encoders 235 on the tracks 125 and/or the translating table 120 may be included to measure the location and/or the rotation of the object 130 during scanning. Also, a display 240 may be included to further simplify the control of the system 100 by an operator or to provide preliminary representations or reconstructed images of objects scanned by the system 100.

The various values stored by the memory circuit 215 and/or calculated by the processor circuit 210 will be described with reference to FIGS. 3 and 4. These values include a source-to-detector distance, a source-to-object distance, a translation-step distance, a detector pitch value, a detector type, at least one channel angle, a fan angle, a translation center, a perpendicular-ray-value, a number-of-translation-steps value, and a number-of-views-per-rotation value. The X-ray source 110 typically emits a fan 310 of X-rays through the path of the translating table 120 detected by detector 115. The translating table 120 rotates about a rotation axis, typically in the center of the translation table 120. The rotation axis, if centered on a translation table that transverses in a straight line across the fan 310, will travel along the line as indicated by arrow 320. The perpendicular ray 330 is the line that passes through the source 110 that is perpendicular to the translation path 320. The source-to-object distance is the distance from the source 110 to the rotation axis of the translating table 120 along the perpendicular ray 330.

The source-to-detector distance is the distance between the source 110 and the detector 115. As known in the art, a detector 115 for a typical CT scanning system will include a plurality of detector elements where each element creates an electrical signal that can be collected by the data collector 205. The elements may be provided in a number of forms known in the art such as scintillation crystals, gas chambers, continuous detectors with transistor elements, and so forth. The detector 115 typically includes a plurality of detector channels, collectively labeled with reference numeral 340, with a detector element in each channel. The number of elements or channels in a detector 115 is the number-of-detector-elements value stored or input into the memory circuit 215 for use by the scan determination and/or resampling method.

Figure 3:
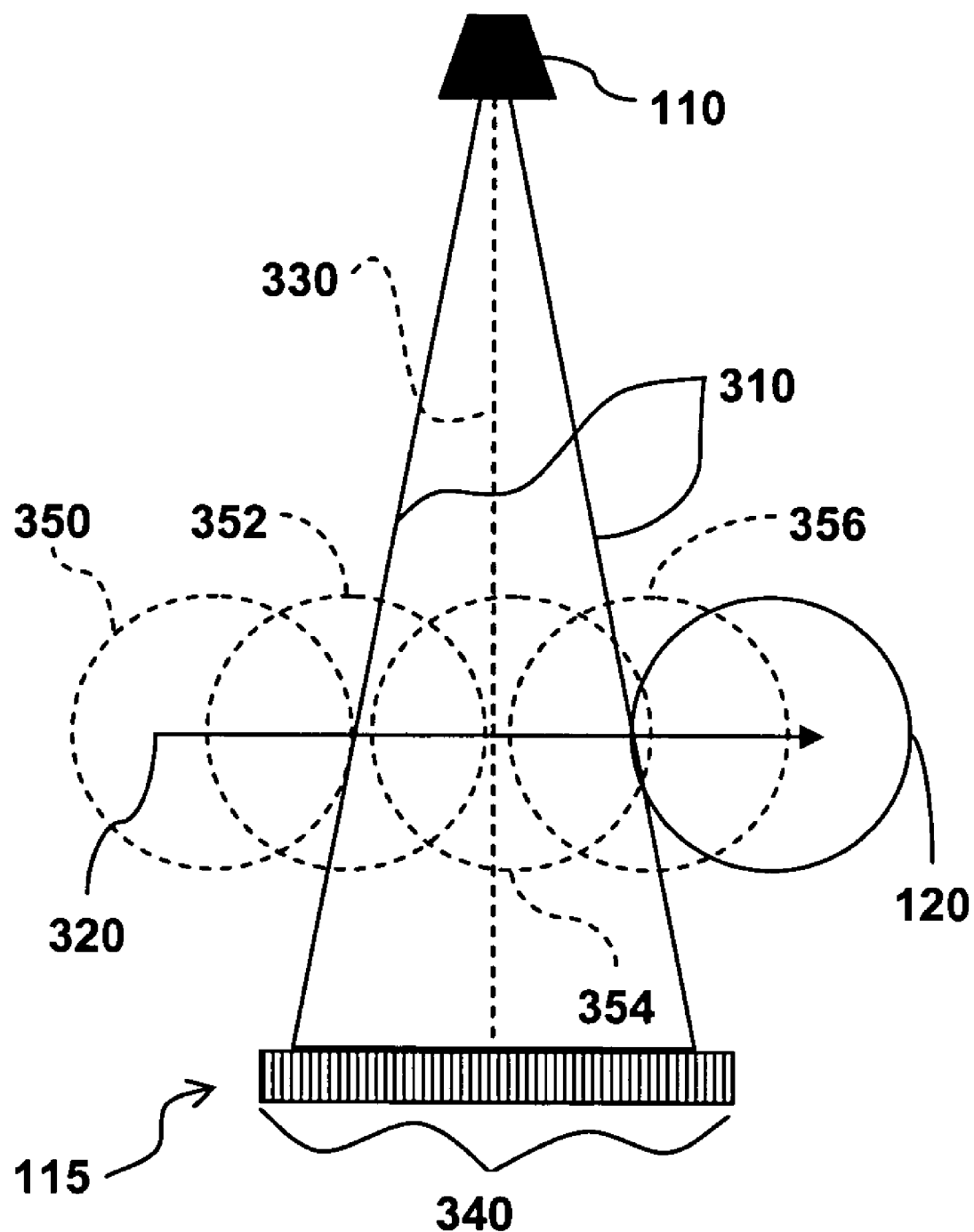
FIG. 3 is a plan view representation of a source of X-rays, detector array, and translating table as the table moves across the fan of X-rays in a second-generation type configuration.
Figure 4:
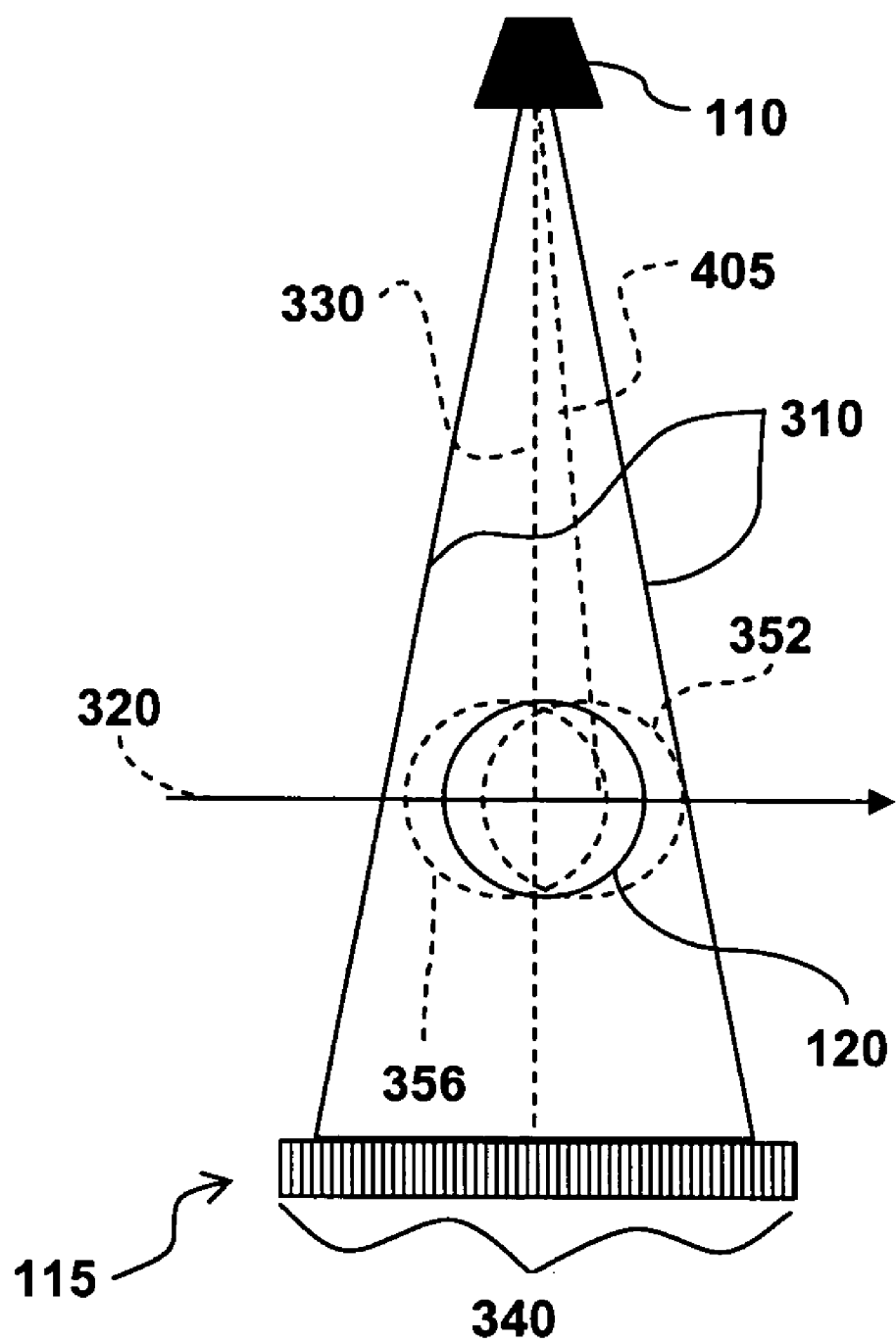
FIG. 4 is a plan view representation of a source of X-rays, detector array, and translating table as the table moves across the fan of X-rays in a third-generation type configuration.

The plurality of detector channels 340 may be curved, often to approximately match the shape of the fan 310, or may be aligned in a straight line as depicted in FIGS. 3 and 4. Alternatively, the detector channels 340 may be arranged in a polygonal approximation of a curved detector 115. These detector 115 shapes are considered the detector shape profile or detector type that is stored or input into the memory circuit 215 for use by the scan determination and/or resampling method. The value of the source-to-detector distance will depend on which portions of the detector 115 geometry are used to measure the distance, for example the distance from the source to the front of the closest detector element, the average distance between the source and a predetermined portion of each detector element, and so forth as known by those in the art. These values are typically provided by the manufacturer of the system 100, may be measured and input through the input device 230 by a user, or may be determined by the system 100 using known algorithms.

The perpendicular-ray-value is the index of the channel where the perpendicular ray 330 intersects the detector 115. As the perpendicular ray 330 will usually not fall directly at the center of a detector element, the perpendicular-ray-value is often not an integer. The perpendicular-ray-value may be provided by the manufacturer of the system 100, may be measured and input through the input device 230 by a user, or may be determined by the system 100 using known algorithms.

The detector pitch value is the distance from a predetermined portion of one detector element in the plurality of detector channels 340 to the middle of the next detector element and may include horizontal and vertical components. This value is a typically a constant dependant on the geometry of the detector 115. The predetermined portion of the detector element used to determine the detector pitch value should be the same predetermined portion used to determine the source-to-detector distance. Typically the detector pitch value is input into the system by an operator or by the manufacturer of the system 100.

The fan angle is the angle between the ray drawn from the source 110 to the first detector element (channel 0) and the ray drawn from the source 110 to the last detector element (channel N−1). The fan angle may be provided by the manufacturer of the system 100, may be measured and input through the input device 230 by a user, or may be determined by the system 100 using known algorithms.

The detector pitch value, source-to-detector distance, perpendicular-ray value, and detector type, assuming a perfectly shaped (curved or flat or polygon) detector 115, may be used to calculate the channel angles indicating, for each of the plurality of detector channels 340, the angle between the perpendicular ray 330 and a ray drawn from the source 110 to the detector channel. Alternatively, the fan angle and perpendicular-ray value, assuming a perfectly shaped (curved or flat or polygon) detector 115, may be used to calculate the channel angles. Alternatively, these angles may be directly measured through known calibration algorithms.

The translation center is the translation distance value of where the translation table rotation axis intersects the perpendicular ray 330. As used herein, the term "ray" indicates a projection from the source 110 to a point on the detector 115, typically a particular channel element. Depending on the portion of the resampling algorithm at issue as understood by those skilled in the art, a ray may refer to the data taken by a channel element such that the ray is a projection of the line of points through which imaging radiation passed through the object 130.

The translation-step distance is the amount of distance traveled in a lateral movement by the translating table 120 in between data collections by the scanning system 100. In some scanning systems 100, the translating table 120 will move a set distance, stop, and the scanner will take a measurement before moving the translating table 120 to the next stop. For example, the translating table 120 may make several stops 350, 352, 354, and 356 across the fan 310 to collect data as seen in FIG. 3. Alternatively, the translating table 120 may move continuously through the fan 310 with the system's 100 collecting data when the translating table 120 is at several points 350, 352, 354, and 356. In another alternative, the system 100 may collect data during the object's 130 movement through the system such that the data is considered to have an effective position of collection or effective data collection point 350, 352, 354, or 356. The distance between the data collection points 350, 352, 354, and 356 is the translation-step distance. This value may be determined as described herein, based on a preprogrammed scanning algorithm, or be determined by reading the distance traveled from the encoders 235 on the tracks 125.

The number-of-translation-steps value is the number of translation steps for or snapshots taken of the object 130 as it passes through the fan 310. Similarly, the number-of-views-per-rotation value is the number of views or snapshots of the object 130 taken while the object 130 rotates.

Figure 5:
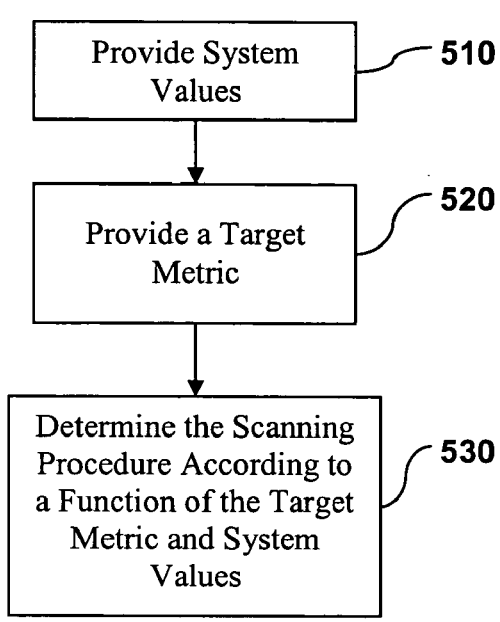
FIG. 5 is a flow diagram for a method as configured in accordance with various embodiments of the invention.

Various methods of using the above described apparatus will be described with reference to FIG. 5. First, CT scanning system geometry dependant values are provided 510 either by manual input, automatic detection, or presetting by the manufacturer or installer. Also, a target metric for the scan is provided 520, typically by a user's inputting the specific metric. The system may determine 530, in an automatic calibrator 220, a CT scanning procedure according to a predetermined function of the target metric and the CT scanning system geometry dependent values. The target metric is often either a target resolution or a target scan time such that the system determines an optimum scanning procedure given the particular target resolution or scan time.

Determining a scanning procedure can apply both to the physical scanning procedure of the object 130 and the data processing procedure of the automatic calibrator 220. For example, in one embodiment, determining the CT scanning procedure may include determining one of the group of values including a number-of-translation-steps value, a number-of-views-per-rotation value, and a translation-step distance according to a predetermined function of the other values of the group of values and the geometry dependant values regarding the CT scanning system. To provide a target resolution, a user will often elect to oversample an object 130 by a certain amount to provide the desired resolution. Surprisingly, however, when shifting the translation table 120 by an amount corresponding to 8× oversampling, the best results may occur by shifting the translation table 120 more than eight times.

Figure 6:
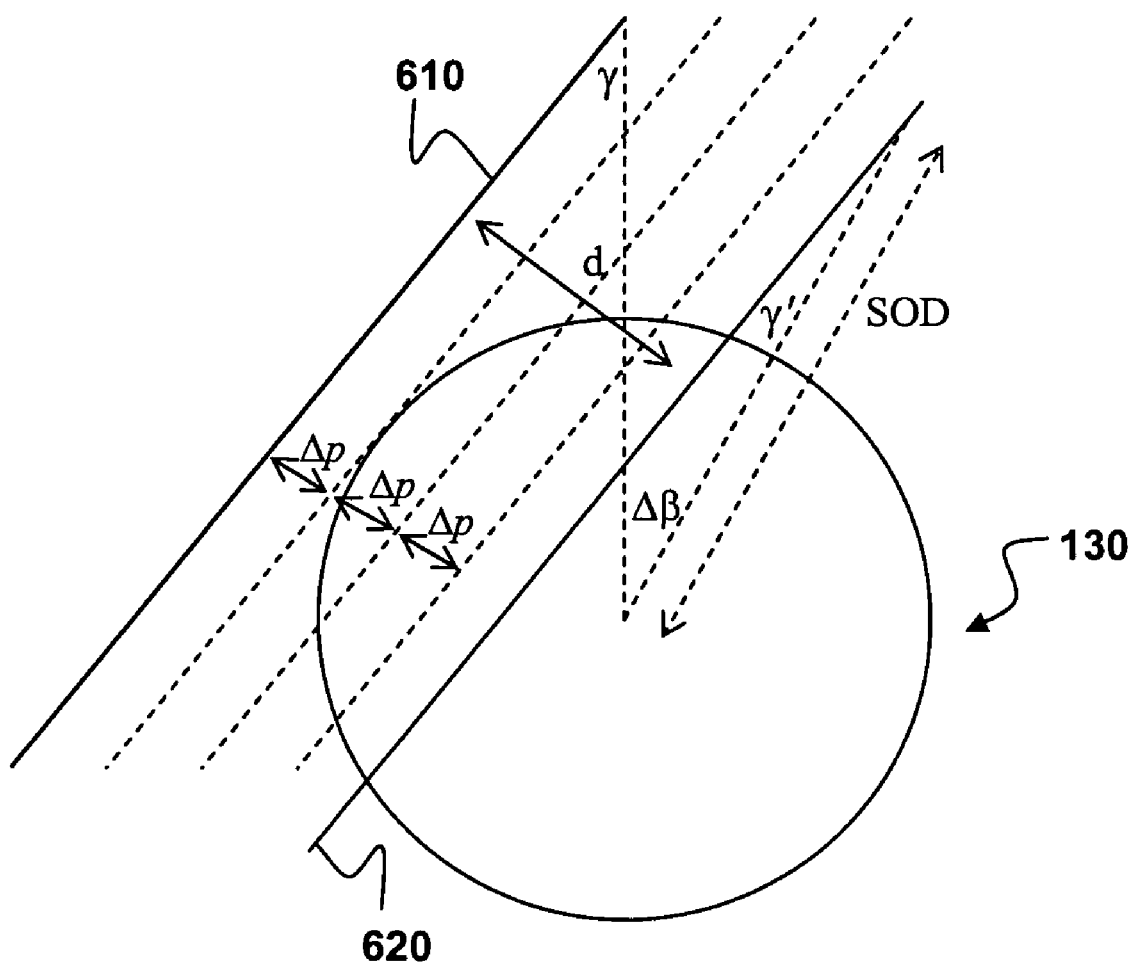
FIG. 6 is a plan view representation of a scanned object and of rays incident on the scanned object in accordance with various embodiments of the invention.

Such an embodiment for calculating the scanning procedure will be described with reference to FIG. 6. The example described below uses a parallel geometry as the preferred output geometry. Consider a ray 610 incident at angle $\gamma$. Suppose the object 130 rotates by an amount $\Delta\beta$, or, equivalently, the source 110 as seen from the translation table 120 or object 130 moves by $\Delta\beta$. Now the new ray 620 parallel to the old ray 610 is at angle $\gamma'=\gamma-\Delta\beta$. Because the translation position of a ray is $p=SOD\times\sin(\gamma)$, the translation-distance between parallel rays is $d=SOD\times|\sin(\gamma')-\sin(\gamma)|$ where SOD is the source-to-object distance. If $\Delta\beta$ is small, then $d\approx SOD\times\Delta\beta\times\cos(\gamma)$. If the number-of-translations-steps is $N_{tranpos}$ and the translation-step distance is $\Delta p$, then to acquire data over the difference d without missing a viewing angle, the number of translations is $$N_{tranpos} \geq \frac{SOD \times 2\pi}{\Delta p \times ViewsPerRev}$$

where ViewsPerRev is the number-of-views-per-rotation value assuming a 360° revolution. This last equation, therefore, describes the relationship among the values of the number-of-translation-steps value, the number-of-views-per-rotation value, and the translation-step distance such that when provided two of these values and scanning system geometry values sufficient to determine the source-to-object distance, the third value may be determined by the automatic calibrator 220.

As expected, if one halves the translation-step distance, one should double the number of number-of-translation-steps value. The above equation, however, also indicates that when halving the number-of-views-per-rotation value, one should also double the number-of-translation-steps value. Similarly, the required number-of-translation-steps increases with the source-to-object distance. When fewer translation steps than required are used, often a gap appears such that to provide enough data for a representation of the object, one must use acquired data from a ray from either a significantly distant translational position or a significantly distant viewing direction $\gamma$.

For example, at a given source-to-object distance, the table below shows the minimum requirement of the number-of-translation-steps value $N_{tranpos}$ for a given translation-step distance $\Delta p$ according to the above equations. Note that in all of these cases, $N_{tranpos}$ is larger than the oversampling factor (the ratio of $\Delta p$ to detector pitch). The detector pitch is 1.5 mm in this example.

TABLE 1

Minimum $N_{tranpos}$ required for SOD = 2930 mm

| | $\Delta p$ (oversampling factor) | | | |
| --- | --- | --- | --- | --- |
| ViewsPerRev | 0.147 mm (8×) | 0.0980 mm (12×) | 0.0735 mm (16×) | 0.0367 mm (32×) |
| 9216 | 14 | 21 | 28 | 55 |
| 5760 | 22 | 33 | 44 | 87 |
| 4096 | 31 | 46 | 62 | 123 |
| 3072 | 41 | 62 | 82 | 164 |
| 2048 | 62 | 92 | 123 | 245 |

For a desired view angle and translation position, ($\theta$, t), in an output data set or array in a parallel geometry, one may interpolate from a fan-beam sample (or samples) of acquired data with coordinates ($\beta$, $\gamma$, $\nu$) for the acquired data array, where $\nu$ is displacement. Typically, acquired data points that are near to the desired view angle and translation position, ($\theta$, t) in parallel coordinates, are chosen such that $\hat{t}$ ($\beta$, $\gamma$,$\nu$)=SOD $\sin\gamma$+$\nu$ $\cos\gamma$ and $\hat{\theta}$ ($\beta$,$\gamma$,$\nu$)=$\beta$+$\gamma$. The geometrical error, $e(\theta,t,\hat{\theta},\hat{t})$, between the desired output data set and available acquired data points can be expressed as the area lying between the two projection beams. At a radius R, the error is $e=(t-\hat{t})+R\sin(\theta-\hat{\theta})$. If $\theta$ is in radians, this error is approximately $e\approx(t-\hat{t})+R\times(\theta-\hat{\theta})$. For an available beam geometry, the error e may be written as a function of view angle and translation position, ($\theta$, t). Therefore, the average error may be calculated over some region of the output data array, typically a sinogram.

The error may also be referred to as the sampling density such that a sufficient number of data points are acquired during a scan to populate a target output data set. The sampling density, D (more precisely, density is 1/D), may be calculated for a given scan using the following equations:

$$D_{mean} = \frac{1}{A}\int_{\theta,t}|e| \text{ and } D_{rms} = \sqrt{\frac{1}{A}\int_{\theta,t}|e|^2}$$

where A is the area of the sinogram over which the data is integrated. The integrations can in special cases be done analytically but is are general are done as approximations by summing over a fine grid.

Sampling density is evaluated as a function of three main parameters: the number-of-views-per-rotation for a 360° revolution, the oversampling factor (defined as the ratio of the detector pitch (projected at isocenter) to the translation-step distance), and the number-of-translation-steps value. Additionally, sampling density depends on several other CT scanning system geometry dependant parameters. The table below shows the error for a variety of data acquisition scans.

The parameter values for this example are as follows: SOD=2932.37, source-to-detector distance (SID)=3739.13, detector pitch=1.5 mm (at the detector), and the average radius of the point of interest on the object 130 from the center of rotation for the object 130, here R=200 mm. The grid used to approximate the integration extended over the intervals t∈[−20.48 mm, 20.48 mm] and θ∈[90°, 91.1°], with spacing dt=0.005 mm and dθ=0.011°, although those skilled in the art will recognize that other parameters may be used in various scanning systems and situations. The small sampling interval in view angle θ is justified because the density of views should not change as a function of the view angle θ.

per revolution, i.e. the number-of-views-per-rotation value, and the number of position, i.e. the number-of-translation-steps value. Similarly, Table 2 demonstrates how a target scan time may include a minimum scan time attainable to obtain a target resolution. Thus, using the above described system will allow a user to obtain a quality scan image using a proscribed or faster scanning method.

Based on the above, the preferred strategy for determining the scanning procedure for data acquisition includes the following: choose the translation-step distance $\Delta p$ based on the target resolution, choose a number-of-views-per-rotation

TABLE 2

Sampling Density for different acquisitions

| Views per Revolution | Oversampling Factor | Number of Positions | Terror (mm) mean | Terror (mm) rms | θ error (deg) mean | θ error (deg) Rms | Combined error D (mm) mean | Combined error D (mm) rms |
|---|---|---|---|---|---|---|---|---|
| 9216 | 8 | 8 | 0.0693 | 0.0811 | 0.01849 | 0.02163 | 0.1338 | 0.1456 |
| 9216 | 8 | 16 | 0.0679 | 0.0798 | 0.00972 | 0.01149 | 0.1018 | 0.1121 |
| 9216 | 16 | 8 | 0.1853 | 0.2682 | 0.01871 | 0.02183 | 0.2506 | 0.3199 |
| 9216 | 16 | 16 | 0.0362 | 0.0426 | 0.01786 | 0.02106 | 0.0985 | 0.108 |
| 9216+ | 16 | 32 | 0.0346 | 0.0405 | 0.00954 | 0.01132 | 0.0679 | 0.0741 |
| 9216 | 32 | 8 | 0.3298 | 0.4348 | 0.01894 | 0.02204 | 0.3959 | 0.4891 |
| 9216 | 32 | 16 | 0.1601 | 0.2455 | 0.01853 | 0.02167 | 0.2248 | 0.2954 |
| 9216 | 32 | 32 | 0.0189 | 0.0228 | 0.01742 | 0.02065 | 0.0797 | 0.0892 |
| 4096 | 8 | 8 | 0.0731 | 0.0863 | 0.03971 | 0.04693 | 0.2117 | 0.2325 |
| 4096 | 8 | 12 | 0.0725 | 0.0858 | 0.03178 | 0.03908 | 0.1834 | 0.2042 |
| 4096 | 8 | 16 | 0.0697 | 0.0815 | 0.0252 | 0.03119 | 0.1576 | 0.1754 |
| 4096 | 8 | 32 | 0.0679 | 0.0799 | 0.01067 | 0.01246 | 0.1052 | 0.1153 |
| 4096 | 16 | 8 | 0.1886 | 0.2719 | 0.04136 | 0.04845 | 0.333 | 0.3974 |
| 4096 | 16 | 16 | 0.0407 | 0.0522 | 0.03812 | 0.04545 | 0.1738 | 0.195 |
| 4096 | 16 | 32 | 0.0371 | 0.044 | 0.02414 | 0.03012 | 0.1213 | 0.1384 |
| 4096 | 16 | 60 | 0.0352 | 0.0414 | 0.0114 | 0.01374 | 0.075 | 0.0825 |
| 4096 | 16 | 62 | 0.0351 | 0.0414 | 0.01085 | 0.01289 | 0.073 | 0.0799 |
| 4096+ | 16 | 64 | 0.0346 | 0.0406 | 0.01046 | 0.01227 | 0.0712 | 0.0774 |
| 4096 | 16 | 66 | 0.0346 | 0.0406 | 0.01036 | 0.01218 | 0.0708 | 0.0771 |
| 4096 | 32 | 8 | 0.3347 | 0.4399 | 0.04205 | 0.04907 | 0.4815 | 0.5678 |
| 4096 | 32 | 16 | 0.163 | 0.249 | 0.04106 | 0.04817 | 0.3063 | 0.3717 |
| 4096 | 32 | 32 | 0.0221 | 0.033 | 0.03767 | 0.04502 | 0.1536 | 0.1761 |
| 4096 | 32 | 64 | 0.0196 | 0.0247 | 0.02367 | 0.02965 | 0.1022 | 0.1203 |
| 2048 | 8 | 16 | 0.0774 | 0.099 | 0.05904 | 0.07379 | 0.2835 | 0.3256 |
| 2048 | 8 | 32 | 0.0711 | 0.0837 | 0.03347 | 0.04499 | 0.1879 | 0.2195 |
| 2048 | 8 | 64 | 0.0678 | 0.0798 | 0.01078 | 0.01266 | 0.1054 | 0.1156 |
| 2048 | 16 | 16 | 0.0454 | 0.0714 | 0.07469 | 0.08941 | 0.3062 | 0.3506 |
| 16# | 16 | 2500 | 0.0348 | 0.0407 | 0.01082 | 0.01269 | 0.0726 | 0.079 |
| 16 | 8 | many | 0.0735* | | 0.0115* | | 0.1136* | |
| 16 | 12 | many | 0.0490* | | 0.0115* | | 0.0891* | |
| 16 | 16 | many | 0.0367* | | 0.0115* | | 0.0768* | |

Note that the acquisition marked with a "#" is essentially a 16× oversampled second-generation acquisition. To obtain a similar sampling density with more of a third-generation type acquisition, a user can use either of the acquisitions denoted with a "+" above. The data points denoted with a "*" are theoretical values. Note in particular the case using 4096 views with 16×oversampling increment. According to Table 1, a user should need a minimum of 62 translation positions to avoid a sampling gap. According to Table 2, increasing the number of samples improves sampling error, but in this example, diminishing returns set in around 62–64 positions. At this point, the translational sampling error and rotational sampling error are roughly the best attainable, respectively $\Delta p/2$ and $\Delta \gamma/2$. Further, Table 2 demonstrates how a target resolution may include a maximum resolution attainable within a target scan time as derived from the view value that is mechanically desirable, and choose the number-of-translation-steps value according to the equation:

$$N_{tranpos} = \left\lceil \frac{SOD \times 2\pi}{\Delta p \times ViewsPerRev} \right\rceil.$$

Of course, one skilled in the art will recognize that that a user may choose to set any of the three values and calculate the third depending on the circumstance of a given system or scan. In these embodiments, the system will determine the values for the scanning procedure according to the following equations:

$$ViewsPerRev = ceil\left(\frac{SOD \times 2\pi}{N_{tranpos} \times \Delta p}\right) \text{ and } \Delta p = \frac{SOD \times 2\pi}{ViewsPerRev \times N_{tranpos}}.$$

Sometimes it is more convenient for the user to specify an oversampling ratio rather than translation-step distance. The oversampling ratio is defined as $$Oversample = \frac{detPitch \times \frac{SOD}{SID}}{\Delta p}$$

where detPitch is the detector pitch value such that the system uses the following two formulae to determine the appropriate values:

$$N_{tranpos} = ceil\left(\frac{Oversample \times SID \times 2\pi}{ViewsPerRev \times detPitch}\right)$$

$$ViewsPerRev = ceil\left(\frac{Oversample \times SID \times 2\pi}{N_{tranpos} \times detPitch}\right).$$

Figure 7:
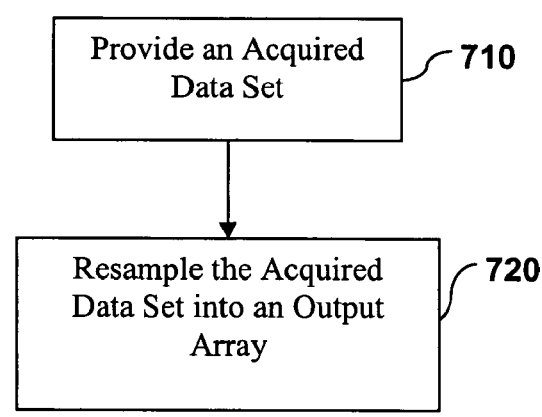
FIG. 7 is a flow diagram for a method as configured in accordance with various embodiments of the invention.

Embodiments for determining a scanning procedure for resampling the acquired data into at least one output array will be described below with reference to FIG. 7. An acquired data set is provided 710, typically through scanning the object 130 to acquire the initial data. The acquired data set is typically dependant on a channel dependant value, a segment dependent value, a rotation-view related number, and a translation-position related number from scanning the object 130 with the CT scanning system. The channel dependent value relates to the horizontal coordinate within the detector of the detector element that captured the particular data point in the acquired data set. The segment dependent value relates to the vertical coordinate within the detector of the detector element which captured the particular point in the acquired data set. In two-dimensional area detectors, "channel" means the column index of the detector element, and "segment" means the row index of the detector element. When the detector includes a plurality of similarly constructed detector element arrays, each detector element array is referred to as a segment, and the element within each segment is referred to as a channel. A detector that has only a single row of fan-beam detectors is called a linear array and has only one segment. The rotation-view related number relates to the view angle or rotational angle of the object 130 when a particular data set is captured. The translation-position related number relates to the translation step at which a particular data set is captured.

The automatic calibrator 220 resamples 720 the acquired data set into at least one output array in the memory circuit 215. The resampling 720 is done through a predetermined sampling algorithm. Typically, the predetermined sampling algorithm provides array parameters for the at least one output array according to the target resolution and a target processing load. The target processing load is a measure of the amount of processing done to the acquired data to provide an output data set suitable for the provision of reconstructed images.

In a typical embodiment using a linear detector, initially, a three dimensional data set is acquired and indexed by channel angle or channel number, translation position, and rotation position. The following description may also apply to systems with two-dimensional detectors where the algorithms apply to each row or segment of the detector. The data is acquired by scanning either in translate-rotate fashion (though maybe with a rotation angle much smaller than the fan) or in rotate-translate fashion (like third-generation CT scanning system oversampling). The predetermined sampling algorithm then resamples the data into a two dimensional parallel data set. To do so, the predetermined sampling algorithm typically provides array parameters including at least one ray-related number and at least one view-related number, and, depending on the embodiment, a segment number, according to the target geometry. The output data array may be used to reconstruct CT scan images.

The resampling algorithm can work with any resampling geometry, preferably a parallel geometry or a fan-beam-related geometry. One skilled in the art will recognize that a parallel geometry will include a virtual parallel geometry or a hypothetical parallel geometry. Similarly, a fan-beam-related geometry will include a virtual or hypothetical fan-beam or cone beam for resampling. These geometries relate to the projection of the rays captured by the detector through the object 130. Preferably, however, the output geometry is chosen in a way that (a) full use is made of the input or acquired data and (b) the output array is as small as possible while still making full use of the acquired data. This philosophy gives rise to the following rules:

$$\Delta t = \Delta p$$

$$N_{views}^{out} \approx \frac{SID \times 2\pi}{detPitch}.$$

The first equation states that the translation-step distance, $\Delta p$, should be the same as the ray spacing in the output data array, $\Delta t$. In terms of the oversampling parameter, as defined above, the latter rule is equivalent to $$N_{views}^{out} \approx \frac{N_{rotpos} \times N_{tranpos}}{Oversampling}$$

where $N_{rotpos}$ is the number-of-views-per-rotation value and $N_{tranpos}$ is the number-of-views-per-rotation value. Thus, the output views should be calculated by one of the following equations:

$$N_{views}^{out} = ceil\left(\frac{SID \times 2\pi}{detPitch}\right)$$

$$= ceil\left(\frac{N_{rotpos} \times N_{tranpos}}{Oversampling}\right).$$

The above rules for $N_{views}^{out}$ are intended for 360° acquisitions, though one skilled in the art may readily modify them to handle other amounts of rotational coverage such as 180° scans. The above rules for $\Delta t$ and $N_{views}^{out}$ are appropriate when the resampling algorithm does not alter the frequency content of the data. Complex interpolation methods known in the art, such as sinc or spline interpolation, preserve frequency information rather well, and thus the above rules are appropriate. Simpler interpolation methods, such as bilinear interpolation, are known to damage high frequency information. To mitigate damage to high frequencies by the interpolation algorithm, the user may choose a resampling grid even finer than that recommended above. For example, when resampling using bilinear interpolation, the best results are typically achieved when $\Delta t$ is half as large as the above rule indicates and $N_{views}^{out}$ is twice as large as the above rules indicate.

To make full use of all the input rays provided in the acquired data, the number of output rays preferably is calculated as $$N_{rays} \approx \frac{SOD \times abs(\sin\gamma[N_{channels} - 1] - \sin\gamma[0])}{\Delta t}$$

where $\Delta t$ is as decided above. The channel angle values $\gamma$ may be parameterized by one skilled in the art by assuming flat or curved detectors. For a curved detector, for example, the above equation becomes $$N_{rays} = ceil\left(\frac{SOD \times abs\left(\sin\frac{FanAngle \times (N_{channels} - 1 - C_{det})}{N_{channels} - 1} + \sin\frac{FanAngle \times C_{det}}{N_{channels} - 1}\right)}{\Delta t}\right)$$

or $$N_{rays} = ceil\left(\frac{SOD \times abs\left(\sin\frac{detPitch \times (N_{channels} - 1 - C_{det})}{SID} + \sin\frac{detPitch \times C_{det}}{SID}\right)}{\Delta t}\right)$$

where $C_{det}$ is the perpendicular-ray value, i.e. the channel index of the perpendicular ray 330. The corresponding choice of central ray value for the output array to make best use of the data is $$C_{ray} = \frac{1}{2} \times \left(N_{rays} - 1 + \frac{SOD}{\Delta t} \times (\sin\gamma[N_{channels} - 1] - \sin\gamma[0])\right);$$

$$C_{ray} = \frac{1}{2} \times \left(N_{rays} - 1 + \frac{SOD}{\Delta t} \times \left(\sin\frac{FanAngle \times (N_{channels} - 1 - C_{det})}{N_{channels} - 1} + \sin\frac{FanAngle \times C_{det}}{N_{channels} - 1}\right)\right);$$

or $$C_{ray} = \frac{1}{2} \times \left(N_{rays} - 1 + \frac{SOD}{\Delta t} \times \left(\sin\frac{detPitch \times (N_{channels} - 1 - C_{det})}{SID} + \sin\frac{detPitch \times C_{det}}{SID}\right)\right).$$

where $C_{ray}$, central ray, is the equivalent of perpendicular ray for the output parallel geometry.

For many reconstruction/backprojection strategies, however, a user may want to limit the system to a symmetric data set, throwing away any asymmetric leftovers. For this case, the user would want $$N_{rays} \approx 2 \times \frac{SOD \times \sin\min\{abs(\gamma[N_{channels} - 1]), abs(\gamma[0])\}}{\Delta t}$$

that, simplified for a curved detector embodiment, is $$N_{rays} = ceil\left(2 \times \frac{SOD \times \sin\left(\frac{FanAngle}{N_{channels} - 1} \times \min\{N_{channels} - 1 - C_{det}, C_{det}\}\right)}{\Delta t}\right)$$

or $$N_{rays} = ceil\left(2 \times \frac{SOD \times \sin\left(\frac{detPitch}{SID} \times \min\{N_{channels} - 1 - C_{det}, C_{det}\}\right)}{\Delta t}\right).$$

For these symmetric choices, the system would preferably use $$C_{ray} = \frac{N_{rays} - 1}{2}.$$

In a typical embodiment, the predetermined sampling algorithm resamples acquired data into the at least one output array using a weighting parameter $\lambda$. The weighting parameter typically balances a relative weight of the ray number parameter and the view number parameter from the scanning data when resampling the acquired data into the at least one output array. Thus, the weighting parameter denotes the relative importance between interpolating from the best view-angle as opposed to interpolating from the best ray-position. Typically, one parameter can only be optimized at the expense of the other. In a typical embodiment, the requirement is that $0 \leq \lambda < \infty$, and a small value (near zero) places most of the emphasis on ray-position, such that the data for the output array is pulled from the closest ray, paying little importance to which view it is from. A large value places most of the emphasis on view position, such that the data for the output array is pulled from the closest view, placing little importance on which ray position it is from.

In particular, the resampling algorithm attempts to minimize the magnitude of the geometrical distance, e, between acquired and resampled rays. The error (distance) between two rays, measured at a point a distance R away from the rotation axis, is calculated as $e=(t-\hat{t})+R\sin(\theta-\hat{\theta})$. If $\theta$ is in radians this is approximately: $e \approx (t-\hat{t})+R\times(\theta-\hat{\theta})$ where t and $\theta$ are ray-position and ray-angle, respectively, and hats indicate the positions of original acquired data, and without-hats are for resampled data in the output array. The weighting parameter $\lambda$ in this embodiment essentially specifies an effective radius R at which to measure distance e.

Therefore, when $\theta$ and $\gamma$ are expressed in radians, the best value for $\lambda$ for a given target point in the reconstructed image is the distance of that point from the rotation axis. Because each ray affects a line of points through the image, and each ray has a different distance from the rotation axis, this optimal $\lambda$ can not be used everywhere. Based on the expected object size, however, the value may be found that gives the best worst-case performance or the best typical (or average) performance. In this way, the weighting parameter may be calculated automatically as a function of the scanning field of view.

For example, "FOV" denotes the scan-field-of-view radius, i.e. the maximum radius away from the axis of rotation for which all points within that radius are always covered by at least one ray from every rotation position. Mathematically, this may be represented as $$FOV = SOD \times \sin\min\{abs(\gamma[0]), abs(\gamma[N_{channels}])\}$$

where the best worst-case value of $\lambda$ is $\lambda$=FOV and the best typical-case value of $\lambda$ is $\lambda$=FOV/2. One skilled in the art will realize that the above calculations of FOV and $\lambda$ for symmetric scans can be modified appropriately for asymmetrically truncated scans, where the rotation axis lies near one edge of the fan.

Resampling also typically depends on a list of channel angles, $\gamma$[channel]. These angles are either measured through a calibration procedure, or determined from the manufactured geometry, or some compromise between these two. When the detector 115 is assumed to be curved and focused on the source 110, the angles are parameterized by perpendicular-ray value and either fan angle or both detector pitch and source-image-distance:

$$\gamma[\text{channel}] = (\text{channel} - C_{det}) \times \frac{detPitch}{SID}$$
$$= (\text{channel} - C_{det}) \times \frac{FanAngle}{N_{channels}}$$

Similar equations can be straightforwardly derived by those skilled in the art for flat or polygon detector arrays.

Typically, the predetermined function for resampling the data includes a resampling algorithm that generates each datum in the output data array by interpolating from data values in the acquired data set that correspond to at least one ray whose ray-path is most similar to a target ray in the output data array. In one embodiment using a direct resampling method, first, the positions of each input sample must be found in the coordinates of the output grid. Though this is shown separately here, this can be combined with the following resampling algorithm:

```
for rotidx = 0 to N_rotpos do
    for tranidx = 0 to N_tranpos do
        for chidx = 0 to N_channels do
            Calculate positions in target parallel geometry:
                p[tranidx,rotidx] = p_meas[tranidx,rotidx] − p_cent
                θ[chidx,tranidx,rotidix] = β[tranidix,rotidix] + γ[chidx]
                f[ch,tranidx,rotidx] = SOD × sin γ[chidx] + p[tranidx,rotidx] × cos γ[chidx]
        end
    end
end
``` where rotidx is the rotation index, tranidx is the translation step index, chidx is the channel index, and p is the translation position of the translation table 120, typically as measured through the encoders 235, $p_{cent}$ is the translation center of the translation table 120 (i.e. the measured table position when the table is in a position where the ray from the source through the rotation axis is perpendicular to the translation axis), and $\beta$ is the rotational position of the translation table 120 (i.e. how far the table is rotated).

Next, the actual resampling may be performed using a variant of bilinear interpolation. It should be noted that the main complication of the direct approach is the "Search for the values of . . . " operation, which may be done a variety of ways. A fast way of implementing this search is given in the lookup table method described below. The direct resample algorithm is:

```
For view = 0 to N^out_view − 1 do
    Calculate θ[view] = β_0 + (2π / N^out_views) × view For ray = 0 to N_rays − 1 do
    Calculate t[ray] = Δt × (ray − C_ray)

For view = 0 to N^out_view − 1 do

For ray = 0 to N_rays −1 do
        Search for the values of (chidx,stepidx,rotidx) which give the
        smallest error-distance which is calculated as:
            d[channel,tranidx,rotidx] = abs (f̂[chidx,stepidx,rotidx] −
                                        t[ray]) + λ × abs
                                        (θ̂[chidx,stepidx,rotidx] − θ[view])
        Find the minimum error-distance separately in each of the four
        directions:
            1. For t̂ ≤ t, θ̂ ≤ θ, find
               (chidx_aa, tranidx_aa, rotidx_aa) and minimum-distance d_aa
            2. For t̂ ≥ t, θ̂ ≤ θ, find
               (chidx_ba, tranidx_ba, rotidx_ba) and minimum-distance d_ba
            3. For t̂ ≤ t, θ̂ ≥ θ, find
               (chidx_ab, tranidx_ab, rotidx_ab) and minimum-distance d_ab
            4. For t̂ ≥ t, θ̂ ≥ θ, find
               (chidx_bb, tranidx_bb, rotidx_bb) and minimum-distance d_bb
        Then calculate interpolation weights
            f_aa = d_ba × d_ab × d_bb
            f_ab = d_aa × d_ba × d_bb
            f_ba = d_aa × d_ab × d_bb
            f_bb = d_aa × d_ab × d_ba
            f_tot = f_aa + f_ab + f_ba + f_bb
            w_aa = f_aa/f_tot
            w_ab = f_ab/f_tot
            w_ba = f_ba/f_tot
            w_bb = f_bb/f_tot
```

-continued

```
at boundary points, where pixel_xx doesn't exist, set d_xx = 1 and
f_xx = 0
Now apply the weights to perform the interpolation:

Q[ray, view] = w_aa × P[chidx_aa, tranidx_aa, rotidx_aa] +
                   w_ba × P[chidx_ba, tranidx_ba, rotidx_ba] +
                   w_ab × P[chidx_ab, tranidx_ab, rotidx_ab] +
                   w_bb × P[chidx_bb, tranidx_bb, rotidx_bb]
    end
end
``` where Q is the output array or resampled data.

Often, a large detector 115 may have several malfunctioning channels, and typically, data from these channels should be thrown away. Rather than doing so before or after the resampling algorithm, this filtering may be done by providing the resampling algorithm with a "bad channel" list and making the resampling algorithm not consider malfunctioning channels while looking for the best samples in the step "Find the minimum error-distance separately in each of the four directions . . . "

The above variant of bilinear interpolation could straightforwardly be replaced by any resampling algorithm known in the art for resampling from a set of irregular points, in this case $P(\hat{\theta},\hat{t})$, onto a regular grid, in this case $Q(\theta,t)$.

In another embodiment, the resampling algorithm is executed using a predetermined table including at least one coordinate offset and at least one interpolation weight. The typical lookup table method includes of two steps: 1) pre-calculate an interpolation table, and 2) resample the data using the interpolation table from Step 1. In this approach, much of the computation can be offloaded into the first step and therefore reused, saving much of the processing power needed per scan. In addition, the second step can be done concurrently while acquired data is still arriving. This embodiment operates upon several conditions including that the translation table positions do not change with rotation position or during rotation:

$$p_{meas}[stepidx, rotidx] = p_{meas}[stepidx]$$

Also, the rotation increment should stay constant and divisible into 360°, and all the rotations should start from the same position:

$$\beta[stepidx, rotidx] = \beta_0 + rotidx \times \Delta\beta$$

where $$\Delta\beta = \frac{360°}{N_{rotpos}}.$$

Finally, the number of output views should be an integer multiple of the number of input rotational-view positions: $N_{views}^{out}$=upsampleViews×$N_{rotpos}$, where upsampleViews is an integer $\geq 1$. When these conditions are satisfied, the resampled array produced by this embodiment is identical to the array produced by the direct embodiment described above.

An example of generating the lookup table is as follows. First, a table of acquired ray-positions, $\hat{t}$, is created, optionally giving special treatment to prevent the algorithm from interpolating from any malfunctioning channels (through use of a user-supplied "bad channel list"). The following algorithm is typically employed for this step:

```
for tranidx = 0 to N_tranpos do
    p[tranidx] = p_meas [tranidx] - p_cent
    for channel = 0 to N_channels do
        t̂[channel,         ⎧ SOD × sin γ [channel] -            channel is
        stepidx]      =    ⎨ p[stepidx] × cos γ[channel],       functioning properly
                           ⎪ very large negative                channel is
                           ⎩ number << -FOV,                    malfunctioning
    end
end
```

Then, the table is sorted in terms of increasing $\hat{t}$, so tbl_t[i] is the sorted $\hat{t}$ and tbl_channel [i] and tbl_tranpos[i] are the indices relating tbl_t to $\hat{t}$. In other words, $\hat{t}$ is sorted to generate tbl_t, tbl_channel, and tbl_tranpos such that tbl_t[i+1]$\geq$tbl_t[i] for all i and tbl_t[i]=$\hat{t}$ [tbl_channel[i], tbl_tranpos[i]]. Next, the tables $w_{aa}$, $w_{ab}$, $w_{ba}$, $w_{bb}$, chidx$_{aa}$, chidx$_{ab}$, chidx$_{ba}$, chidx$_{bb}$, tranidx$_{aa}$, tranidx$_{ab}$, tranidx$_{ba}$, tranidx$_{bb}$, rotofs$_{aa}$, rotofs$_{ab}$, rotofs$_{ba}$, rotofs$_{bb}$, are allocated with each having the dimensions $N_{rays}$×upsampleViews. Then, the weight and index tables are created using the following preferred algorithm:

Initialize $t_{win}$. Currently, we use $t_{win}$=abs($\Delta$p)×2.2

```
For viewmod = 0 to (upsampleViews-1) do
    Set θ_mod = viewmod × Δθ + β_0
    Set c_a = 0
    While tbl_t[c_a] <= (very large negative number),
        c_a = c_a + 1
    end
    Set c_b = c_a
    For ray = 0 to (N_rays - 1) do
        Set t = (ray-Cray) × Δt
        While (c_a < N_channels × N_tranpos - 2 ) and
            (tbl_t[c_a + 1] + t_win < t), c_a = c_a + 1
        While (c_b < N_channels × N_tranpos - 1 ) and
            (tbl_t[c_b + 1] + t_win < t), c_b = c_b + 1
        (note, at this point, tbl_t[c_a]+t_win < t < tbl_t[cb]-t_win)
        For c = c_a to c_b do
```

$$\delta_{view}^{ideal}[c] = \frac{(\theta_{mod} - \gamma[tbl\_channel[c]])}{\Delta\beta} - round\left(\frac{\theta_{mod} - \gamma[tbl\_channel[c]]}{\Delta\beta}\right)$$

$$\delta_{view}^{a} = floor(\delta_{view}^{ideal})$$

$$\delta_{view}^{b} = \delta_{view}^{a} + 1$$

$$d_a[c] = abs(tbl\_t[c] - t[ray]) + \lambda \times \Delta\beta \times (\delta_{view}^{ideal} - \delta_{view}^{a})$$

$$d_b[c] = abs(tbl\_t[c] - t[ray]) + \lambda \times \Delta\beta \times (\delta_{view}^{a} - \delta_{view}^{ideal})$$

```
    end
    Find the minimum error-distance separately in each of the four
    directions:
    1. For t̂[c] ≤ t, find c_aa for which distance d_a is smallest,
    save distance as d_aa
    2. For t̂[c] ≥ t, find c_ba for which distance d_a is smallest,
    save distance as d_ba
    3. For t̂[c] ≤ t, find c_ab for which distance d_b is smallest,
    save distance as d_ab
    4. For t̂[c] ≥ t, find c_bb for which distance d_b is smallest,
    save distance as d_bb
    Then calculate interpolation weights
        f_aa = d_ba × d_ab × d_bb
        f_ab = d_aa × d_ba × d_bb
        f_ba = d_aa × d_ab × d_bb
        f_bb = d_aa × d_ab × d_ba
        f_tot = f_aa + f_ab + f_ba + f_bb
        w_aa[ray,viewmod] = f_aa/f_tot
        w_ab[ray,viewmod] = f_ab/f_tot
        w_ba[ray,viewmod] = f_ba/f_tot
        w_bb[ray,viewmod] = f_bb/f_tot
    and save the source pointers for xy equal to each of
    aa, ab, ba, bb:
        chidx_xy[ray,viewmod] = tbl_channel[c_xx]
        tranidx_xy[ray,viewmod] = tbl_tranpos[c_xx]
        rotofs_xy[ray, viewmod] = δ_view^y[c_xy]
    end
end
```

Another implementation includes interpolating data using a lookup table for second-generation scanning systems. This embodiment is amenable to translate-rotate scanning, where data is acquired at all the translation-positions, then the table is rotated slightly, and a full translation of the data is acquired. With the example algorithm below, data may be processed from the previous rotational-positions concurrently while acquiring further data.

```
for view = 0 to (N_view^out − 1) do
    Set viewmod = (view mod upsampleViews)
    for ray = 0 to (N_rays − 1) do
        rotbase = floor( view / upsampleViews )
        Q[ray,view] =  w_aa[ray,.viewmod] ×
          P[chidx_aa[ray,.viewmod],tranidx_aa[ray,.viewmod],
          mod(rotbase+rotofs_aa,ViewsPerRev)] +
            w_ba[ray,.viewmod] × P[chidx_ba[ray,.viewmod],
            tranidx_ba[ray,.viewmod],mod(rotbase+rotofs_ba,
            ViewsPerRev)] +
            w_ab[ray,.viewmod] × P[chidx_ab[ray,.viewmod],
            tranidx_ab[ray,.viewmod],mod(rotbase+rotofs_ab,
            ViewsPerRev)] +
            w_bb[ray,.viewmod] × P[chidx_bb[ray,.viewmod],
            tranidx_bb[ray,.viewmod],mod(rotbase+rotofs_bb,
            ViewsPerRev)]
    end
end
```

Another embodiment includes interpolating data using a lookup table for third-generation scanning systems. This embodiment is amenable to rotate-translate scanning, where the system acquires a full-rotation of data, translates the table, and then acquires another full-rotation, etc. The resampling can be performed for data from previous translational-positions concurrently while we continue to acquire data.

Initialize Q[ray,view]=0 for all ray,view

```
for tranpos=0 to (N_tranpos-1) do,
    for view=0 to (N_view^out-1) do
        Set viewmod = (view mod upsampleViews)
        for ray=0 to (N_rays-1) do
            rotbase = floor( view / upsampleViews )
            for xx = aa, ba, ab, bb do
                if tranidx_xx[ray,viewmod] == tranpos do
                    Q[ray,view] = Q[ray,view] +
                      w_xx[ray,.viewmod]
                      xP[childx_xx[ray,.viewmod],tranidx_xx[ray,.viewmod],mod(rotbase+rotofs_xx, ViewsPerRev)]
        end
end
```

The resampling method and apparatus, therefore, provide assistance to a user of a CT scanning system in deciding upon a scanning procedure. Various system embodiments described herein assist in choosing the acquisition procedure parameters to optimize the speed of acquisition without unduly sacrificing the output image quality. Further, certain embodiments assist in determining the output array parameters to minimize processing time while maximizing the use of the acquired data.

Those skilled in the art will recognize that a wide variety of modifications, alterations, and combinations can be made with respect to the above described embodiments without departing from the spirit and scope of the invention. Such modifications, alterations, and combinations are to be viewed as being within the ambit of the inventive concept.

I claim:

1. A computed tomography ("CT") scanning system comprising:
   an X-ray source;
   a detector disposed opposite the X-ray source;
   a translating table configured to rotate and move an object between the X-ray source and the detector;
   a data collector operably coupled to the detector that collects data from the detector;
   a memory circuit storing geometry dependant values regarding the CT scanning system and a target metric comprising one from a group comprising a target resolution and a target scan time; and
   a processor circuit associated with the data collector and the memory circuit that determines a CT scanning procedure according to a predetermined function of the target metric and the CT scanning system geometry dependant values.

2. The system of claim 1 wherein the processor circuit associated with the memory circuit further determines one of a group of values comprising a number-of-translation-steps value, a number-of-views-per-rotation value, and a translation-step distance according to a predetermined function of other values of the group of values and the geometry dependant values regarding the CT scanning system.

3. The system of claim 1 wherein the values regarding the CT scanning system further comprise at least one of the group comprising:
   a source-to-detector distance;
   a source-to-object distance;
   at least one channel angle;
   a fan angle;
   a detector type;
   a translation center;
   perpendicular-ray-value;
   at least one detector pitch value; and
   a number-of-detector-elements value.

4. The system of claim 1 wherein the processor circuit associated with the memory circuit further provides at least one output data array into which acquired data from each of at least one translation position of the object is fit through a predetermined sampling algorithm.

5. The system of claim 4 wherein the predetermined sampling algorithm interpolates data from the acquired data into the output data array.

6. The system of claim 4 wherein the predetermined sampling algorithm generates each datum in the at least one output data array by interpolating from data values in the acquired data that correspond to at least one ray whose ray-path is most similar to a target ray in the output data array.

7. The system of 6 further comprising executing the resampling algorithm using a predetermined table comprising at least one coordinate offset and at least one interpolation weight.

8. The system of claim 4 wherein the output data array includes parameters comprising at least one target geometry view angle and at least one target geometry ray distance.

9. The system of claim 1 wherein the target geometry is one from a group comprising a parallel geometry and a fan-beam-related geometry.

* * * * *

UNITED STATES PATENT AND TRADEMARK OFFICE
CERTIFICATE OF CORRECTION

PATENT NO. : 7,286,630 B2 Page 1 of 1
APPLICATION NO. : 11/305750
DATED : October 23, 2007
INVENTOR(S) : Kevin Holt It is certified that error appears in the above-identified patent and that said Letters Patent is hereby corrected as shown below:

IN THE CLAIMS:

Claim 7, Column 20, Line 66; Change "6" to -- Claim 6 --.

Signed and Sealed this

Fifteenth Day of April, 2008

JON W. DUDAS
*Director of the United States Patent and Trademark Office*